United States Patent [19]

Chang et al.

[11] 4,188,336

[45] Feb. 12, 1980

[54] CONVERSION OF SYNTHESIS GAS TO AROMATIC HYDROCARBONS

[75] Inventors: Clarence D. Chang, Princeton; William H. Lang, Pennington, both of N.J.

[73] Assignee: Mobil Oil Corporation, New York, N.Y.

[21] Appl. No.: 903,270

[22] Filed: May 5, 1978

Related U.S. Application Data

[63] Continuation-in-part of Ser. No. 825,622, Aug. 18, 1977.

[51] Int. Cl.² .............................................. C07C 1/04
[52] U.S. Cl. ............................ 260/449 R; 260/449 M
[58] Field of Search ....................... 260/449 R, 449 M

[56] References Cited

U.S. PATENT DOCUMENTS

| 4,086,262 | 4/1978 | Chang et al. | 260/449 R |
| 4,096,163 | 6/1978 | Chang et al. | 260/449 R |

*Primary Examiner*—Howard T. Mars
*Attorney, Agent, or Firm*—Charles A. Huggett; Michael G. Gilman; Carl D. Farnsworth

[57] ABSTRACT

Synthesis gas is converted to aromatic hydrocarbons over an intimate mixture of catalysts comprising a first component of $ZnO\text{-}Cr_2O_3$ mixed catalyst, characterized by catalytic activity for the reduction of hydrogen of carbon monoxide, wherein the Zn:Cr atomic ratio is less than about 4:1 and a second component selected from a selective class of acidic crystalline alumino-silicates having a silica:alumina ratio greater than 12:1 and a pore dimension greater than about 5 Angstroms.

5 Claims, 4 Drawing Figures

Syngas Conversion. (Constant Cr/Al)
800°F, 1200 psig. $H_2/CO = 1$, ~1WHSV

CONVERSION OF SYNTHESIS GAS TO AROMATIC HYDROCARBONS

This application is a continuation-in-part of application Ser. No. 825,622, filed Aug. 18, 1977.

BACKGROUND OF THE INVENTION

1. Field of the Invention

This invention is concerned with an improved process for converting synthesis gas, i.e., mixtures of gaseous carbon oxides with hydrogen or hydrogen donors, to hydrocarbon mixtures. This invention is particularly concerned with a process for converting synthesis gas to hydrocarbon mixtures rich in aromatic hydrocarbons. In another aspect, this invention is concerned with providing novel catalysts for the conversion of synthesis gas to hydrocarbon mixtures rich in aromatic hydrocarbons.

2. Prior Art

Processes for the conversion of coal and other hydrocarbons such as natural gas to a gaseous mixture consisting essentially of hydrogen and carbon monoxide, or of hydrogen and carbon dioxide, or of hydrogen and carbon monoxide and carbon dioxide, are well known. Although various processes may be employed for the gasification, those of major importance depend either on the partial combustion of the fuel with an oxygen-containing gas or on the high temperature reaction of the fuel with steam, or on a combination of these two reactions. An excellent summary of the art of gas manufacture, including synthesis gas, from solid and liquid fuels, is given in Encyclopedia of Chemical Technology, Edited by Kirk-Othmer, Second Edition, Volume 10, pages 353–433, (1966), Interscience Publishers, New York, New York, the contents of which are herein incorporated by reference. The techniques for gasification of coal or other solid, liquid or gaseous fuel are not considered to be per se inventive here.

It would be very desirable to be able to effectively convert synthesis gas, and thereby coal and natural gas, to highly valued hydrocarbons such as motor gasoline with high octane number, petrochemical feedstocks, liquefiable petroleum fuel gas, and aromatic hydrocarbons. It is well known that synthesis gas will undergo conversion to form reduction products of carbon monoxide, such as hydrocarbons, and/or oxygen containing compounds such as methanol at from about 300° F. to about 850° F. under from about one to one thousand atmospheres pressure, over a fairly wide variety of catalysts. The Fischer-Tropsch process, for example, which has been most extensively studied, produces a range of liquid hydrocarbons, a portion of which have been used as low octane gasoline. The types of catalysts that have been studied for this and related processes include those based on metals, oxides or other compounds of iron, cobalt, nickel, ruthenium, thorium, rhodium and osmium. Methanol synthesis processes, for example, use catalysts composed of mixtures of two or more oxides and in particular use ZnO base and CuO base mixed catalysts. A review of catalytic processes for the synthesis of methanol from mixtures containing CO and $H_2$ is given in Emmett, P.H., *Catalysis III*, N.Y., Reinhold, 1955. Chapter 8, pages 349–411, by G. Natta, *Synthesis of Methanol*, the text of which is incorporated herein by reference.

The wide range of catalysts and catalyst modifications disclosed in the art and an equally wide range of conversion conditions for the reduction of carbon monoxide by hydrogen provide considerable flexibility toward obtaining selected boiling-range products. Nonetheless, in spite of this flexibility, it has not proved possible to make such selections so as to produce liquid hydrocarbons in the gasoline boiling range which contain highly branched paraffins and substantial quantities of aromatic hydrocarbons, both of which are desired for high quality gasoline, or to selectively produce aromatic hydrocarbons particularly rich in the benzene to xylenes range. A review of the status of this art is given in "Carbon Monoxide-Hydrogen Reactions", Encyclopedia of Chemical Technology, Edited by Kirk-Othmer, Second Edition, Volume 4, pages 446–488 and and Volume 13, pages 370–398. Interscience Publishers, New York, N.Y., the text of which is incorporated herein by reference.

Recently it has been discovered that synthesis gas may be converted to oxygenated organic compounds and these then converted to higher hydrocarbons, particularly high octane gasoline, by catalytic contact of the synthesis gas with a carbon monoxide reduction catalyst followed by contacting the conversion products so produced with a special type of zeolite catalyst in a separate reaction zone. This two-stage conversion is described in copending U.S. patent application, Ser. No. 387,220, filed on Aug. 9, 1973.

Still more recently, it has been discovered that synthesis gas may be converted to hydrocarbon mixtures useful in the manufacture of heating oils, gasoline, aromatic hydrocarbons, and chemical intermediates by catalytic contact with an intimate mixture of: (1) carbon monoxide hydrogen reduction catalyst comprising a methanol synthesis catalyst and (2) a special type of zeolite catalyst comprising an acidic crystalline aluminosilicate having a silica:alumina ratio greater than 12 and a pore dimension greater than about 5 Angstroms. This one-stage conversion is described in copending U.S. patent application Ser. No. 730,871, filed on Oct. 8, 1976.

It is an object of the present invention to provide an improved process for converting fossil fuels to a hydrocarbon mixture that contains large quantities of highly desirable constituents. It is a further object of this invention to provide a more efficient method for converting a mixture of gaseous carbon oxides and hydrogen to a mixture of hydrocarbons. It is a further object of this invention to provide an improved method for converting synthesis gas to a hydrocarbon mixture rich in aromatic hydrocarbons. It is a further object of this invention to provide novel catalysts for the conversion of synthesis gas to a hydrocarbon mixture rich in aromatic hydrocarbons.

BRIEF SUMMARY OF THE INVENTION

It has been discovered that valuable hydrocarbon mixtures may be produced by reacting synthesis gas, i.e., mixtures of hydrogen gas with gaseous carbon oxides, or the equivalents of such mixtures, in the presence of certain heterogeneous catalysts comprising intimate mixtures of at least two components. Copending U.S. patent application Ser. No. 730,871 (referred to above) discloses the selective production of light paraffins from synthesis gas using catalysts comprising a methanol synthesis component and an acidic crystalline aluminosilicate component of selected characteristics. The present invention is based on the further discovery that a class of chromium oxide catalyst with or without the presence of zinc oxide and referred to as a methanol synthesis catalysts, as will be more fully described hereinafter, may be modified such that aromatics are produced when this catalyst is used in conjunction with an acidic crystalline aluminosilicate catalyst of selected characteristic.

It has now been found that aromatics can be synthesized from syngas by shifting the metals ratio of a zinc oxide-chromia catalyst away from an optimum for methanol synthesis; specifically, this is accomplished by providing a Zn:Cr ratio less than about 4:1. When the methanol synthesis catalyst component is mixed with the special acidic crystalline aluminosilicate component herein defined, the catalyst mixture will convert synthesis gas to a mixture of about equal parts of LPG and aromatics with minimal methane production. This intimate catalyst mixture thus produces highly desirable aromatic and LPG products with good selectivity and does so with extraordinarily high conversion per pass. Furthermore, when the preferred class of acidic crystalline aluminosilicate component is used in the intimate mixture, catalytic activity is sustained for unusually long periods of time and the aromatic hydrocarbons produced are rich in toluene and xylene. The catalyst of this invention is also air regenerable and has shift capability.

In yet another aspect, the present invention is based on a further finding in that when the components of the catalyst composition comprising ZnO, $Cr_2O_3$, $Al_2O_3$ and acid ZSM-5 crystalline zeolite are subjected to grinding to obtain an unusually fine state of subdivision (<80 mesh) before mixing and pelleting, the yield of aromatics was markedly increased at the expense of $C_3$ plus (+) paraffins.

DETAILED DESCRIPTION AND PREFERRED EMBODIMENTS

Figure 1:
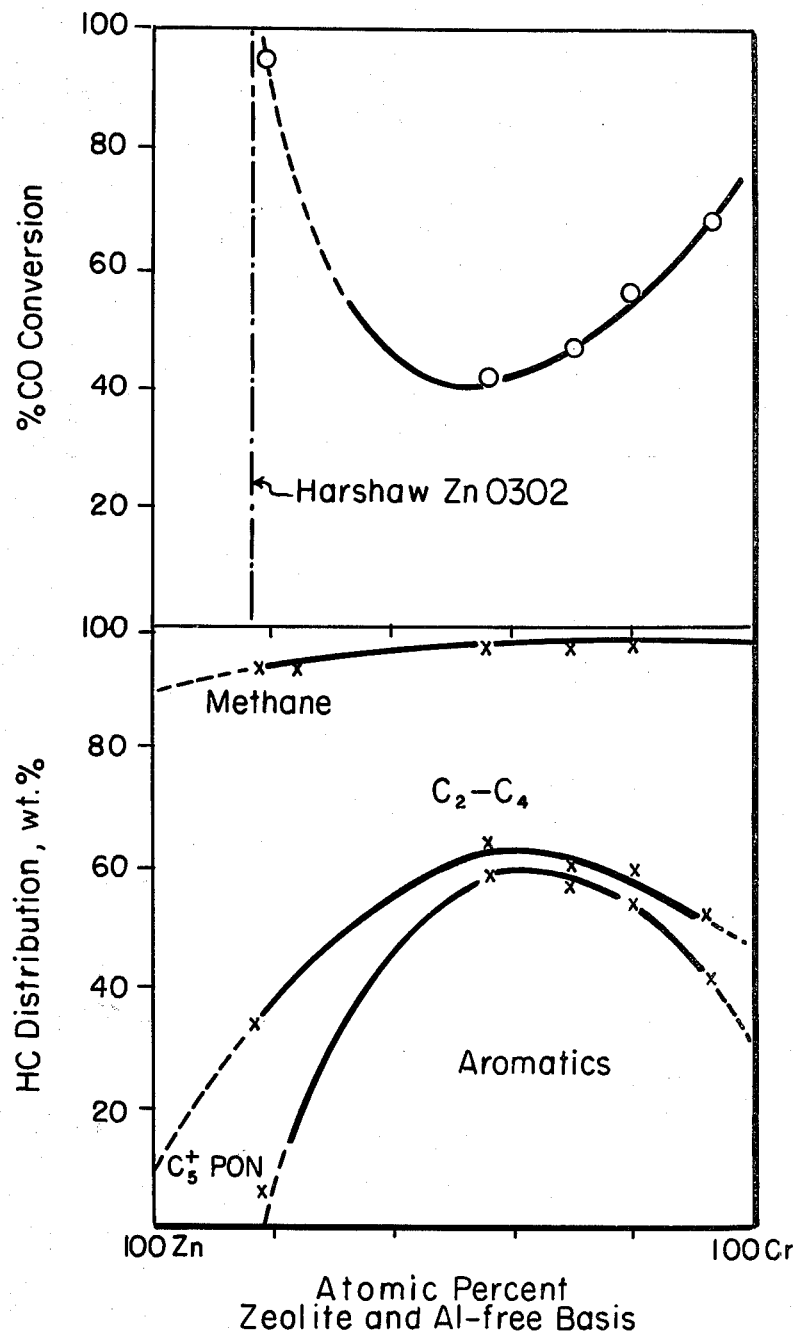

Synthesis gas for use in this invention consists of a mixture of hydrogen gas with gaseous carbon oxides including carbon monoxide and carbon dioxide. By way of illustration, a typical purified synthesis gas will have the composition, on a water-free basis, in volume percentages, as follows: hydrogen, 51; carbon monoxide, 40; carbon dioxide, 4; methane, 1; and nitrogen, 4.

The synthesis gas may be prepared from fossil fuels by any of the known methods, including such in situ gasification processes as the underground partial combustion of coal and petroleum deposits. The term fossil fuels, as used herein, is intended to include anthracite and bituminous coal, lignite, crude petroleum, shale oil, oil from tar sands, natural gas, as well as fuels derived from simple physical separations or more profound transformations of these materials including coked coal, petroleum coke, gas oil, residua from petroleum distillation, and two or more of any of the foregoing materials in combination. Other carbonaceous fuels such as peat, wood and cellulosic waste materials also may be used.

The raw synthesis gas produced from fossil fuels will contain various impurities such as particulates, sulfur, and metal carbonyl compounds, and will be characterized by a hydrogen-to-carbon oxides ratio which will depend on the fossil fuel and the particular gasification technology utilized. In general, it is desirable for the efficiency of subsequent conversion steps to purify the raw synthesis gas by the removal of impurities. Techniques for such purification are known and are not part of this invention. It is preferred to adjust the hydrogen-to-carbon oxides volume ratio to be within the range of from 0.2 to 6.0 prior to use in this invention. Should the purified synthesis gas be excessively rich in carbon oxides, it may be brought within the preferred range by the well-known water-gas shift reaction. On the other hand, should the synthesis gas be excessively rich in hydrogen, it may be adjusted into the preferred range by the addition of carbon dioxide or carbon monoxide. Purified synthesis gas adjusted to contain a volume ratio of hydrogen-to-carbon oxides of from 0.2 to 6.0 will be referred to as adjusted synthesis gas.

It is contemplated that the synthesis gas for use in this invention includes art-recognized equivalents to the already described mixtures of hydrogen gas with gaseous carbon oxides. Mixtures of carbon monoxide and steam, for example, or of carbon dioxide and hydrogen, to provide adjusted synthesis gas by in situ reaction, are contemplated.

The heterogeneous catalysts of this invention comprise at least two components intimately mixed, and in which one component is selected from the class of $ZnO$-$Cr_2O_3$ substances that have catalytic activity for the reduction by hydrogen of carbon monoxide wherein the Zn:Cr atomic ratio is less than than about 4:1, and in which the other component is a class of acidic crystalline aluminosilicate characterized by a pore dimension greater than about 5 Angstroms, a silica-to-alumina ratio of at least 12 and a constraint index within the range of 1 to 12.

The $ZnO$-$Cr_2O_3$ substance or component characterized by catalytic activity for the reduction by hydrogen of carbon monoxide may be selected from any of the art-recognized $ZnO$-$Cr_2O_3$ mixed catalysts for producing hydrocarbons, oxygenated products, or mixtures thereof, from synthesis gas, subject only to the further restriction that the Zn:Cr ratio of the mixed catalyst systems be less than about 4:1. Preferably, the Zn:Cr atomic ratio is within the range from about 3.8:1 to 0:1. Examples of these mixed catalyst systems include mechanical mixtures of $ZnO$ and $Cr_2O_3$, mixtures of $ZnO.Cr_2O_3$ (zinc chromite) and $ZnO$, calcined mixtures of coprecipitated zinc and chromium hydroxides or carbonates, and thermally decomposed mixtures of zinc and chromium acetates.

The $ZnO$-$Cr_2O_3$ mixed catalyst component should in all cases constitute from 0.05 to 99 percent by weight, and preferably from 1 percent to 95 percent of the intimate mixture. The $ZnO$-$Cr_2O_3$ mixed catalyst component may be furnished as elemental metals or as corresponding metal compounds.

The acidic crystalline aluminosilicate component of the heterogeneous catalyst is characterized by a pore dimension greater than about 5 Angstroms, i.e, it is capable of sorbing paraffins having a single methyl branch as well as normal paraffins, and it has a silica-to-alumina ratio of at least 12. Zeolite A, for example, with a silica-to-alumina ratio of 2.0 is not useful in this invention, it has no pore dimension greater than about 5 Angstroms.

The crystalline aluminosilicates herein referred to, also known as zeolites, constitute an unusual class of natural and synthetic minerals. They are characterized by having a rigid crystalline framework structure composed of an assembly of silicon and aluminum atoms, each surrounded by a tetrahedron of shared oxygen atoms, and a precisely defined pore structure. Exchangeable cations are present in the pores.

The catalysts referred to herein utilize members of a special class of zeolites exhibiting some unusual properties. These zeolites induce profound transformations of aliphatic hydrocarbons to aromatic hydrocarbons in commercially desirable yields and are generally highly effective in alkylation, isomerization, disproportionation and other reactions involving aromatic hydrocarbons. Although they have unusually low alumina contents, i.e., high silica to alumina ratios, they are very active even with silica to alumina ratios exceeding 30. This activity is surprising since catalytic activity of zeolites is generally attributed to framework aluminum atoms and cations associated with these aluminum atoms. These zeolites retain their crystallinity for long periods in spite of the presence of steam even at high temperatures which induce irreversible collapse of the crystal framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from, the intra-crystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred zeolites useful in type B catalysts in this invention posses, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful it is preferred to use zeolites having higher ratios of at least about 30. Such zeolites, after activation, acquire an intracrystalline sorption capacity for normal hexane which is greater than that for water, i.e., they exhibit "hydrophobic" properties. It is believed that this hydrophobic character is advantageous in the present invention.

The zeolites useful as catalysts in this invention freely sorb normal hexane and have a pore dimension greater than about 5 Angstroms. In addition, their structure must provide constrained access to some larger molecules. It is sometimes possible to judge from a known crystal structure whether such constrained access exists. For example, if the only pore windows in a crystal are formed by 8-membered rings oxygen atoms, then access by molecules of larger cross-section than normal hexane is substantially excluded and the zeolite is not of the desired type. Zeolites with windows of 10-membered rings are preferred, although excessive puckering or pore blockage may render these zeolites substantially ineffective. Zeolites with windows of twelve-membered rings do not generally appear to offer sufficient constraint to produce the advantageous conversions desired in the instant invention, although structures can be conceived, due to pore blockage or other cause, that may be operative.

Rather than attempt to judge from crystal structure whether or not a zeolite possesses the necessary constrained access, a simple determination of the "constraint index" may be made by continuously passing a mixture of equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10 percent and 60 percent. The mixture of hydrocarbons is passed at 1 liquid hourly space velocity (i.e., 1 volume of liquid hydrocarbon per volume of catalyst per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} (\text{fraction of n-hexane remaining})}{\log_{10} (\text{fraction of 3-methylpentane remaining})}$$

The constraint index approximates the ratio of the cracking rate constants for the two hydrocarbons. Catalysts suitable for the present invention are those which employ a zeolite having a constraint index from 1.0 to 12. Constraint Index (CI) values for some typical zeolites including some not within the scope of this invention are:

| CAS | C.I. |
| --- | --- |
| Erionite | 38 |
| ZSM-5 | 8.3 |
| ZSM-11 | 8.7 |
| ZSM-35 | 6.0 |
| TMA Offretite | 3.7 |
| ZSM-38 | 2.0 |
| ZSM-12 | 2. |
| Beta | 0.6 |
| ZSM-4 | 0.5 |
| Acid Mordenite | 0.5 |
| REY | 0.4 |
| Amorphous Silica-alumina | 0.6 |

The above-described Constraint Index is an important and even critical, definition of those zeolites which are useful to catalyze the instant process. The very nature of this parameter and the recited technique by which it is determined, however, admit of the possibility that a given zeolite can be tested under somewhat different conditions and thereby have different constraint indexes. Constraint Index seems to vary somewhat with severity of operation (conversion). Therefore, it will be appreciated that it may be possible to so select test conditions to establish multiple constraint indexes for a particular given zeolite which may be both inside and outside the above defined range of 1 to 12.

Thus, it should be understood that the parameter and property "Constraint Index" as such value is used herein is an inclusive rather than an exclusive value. That is, a zeolite when tested by any combination of conditions within the testing definition set forth herein above to have a constraint index of 1 to 12 is intended to be included in the instant catalyst definition regardless that the same identical zeolite tested under other defined conditions may give a constraint index value outside of 1 to 12.

The class of zeolites defined herein is exemplified by ZSM-5, ZSM-11, ZSM-12, ZSM-35 and ZSM-38, and other similar materials. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

The subject of ZSM-35 is described in U.S. Pat. No. 4,016,245, the entire contents of which are incorporated herein by reference. The subjet of ZSM-38 is described in U.S. Pat. No. 4,046,859, the entire contents of which are incorporated herein by reference.

The specific zeolites described, when prepared in the presence of organic cations, are substantially catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this special type zeolite; however, the presence of these cations does appear to favor the formation of this special type of zeolite. More generally, it is desirable to activate this type zeolite by base exchange with ammonium salts followed by calcination in air at about 1000° F. for from about 15 minutes to about 24 hours.

Natural zeolites may sometimes be converted to this type zeolite by various activation procedures and other treatments such as base exchange, steaming, alumina extraction and calcination, alone or in combinations. Natural minerals which may be so treated include ferrierite, brewsterite, stilbite, dachiardite, epistilbite, heulandite and clinoptilolite. The preferred crystalline aluminosilicates are ZSM-5, ZSM-11, ZSM-12, ZSM-35 and ZSM-38, with ZSM-5 particularly preferred.

The zeolites used as catalysts in this invention may be in the hydrogen form or they may be base exchanged or impregnated to contain ammonium or a metal cation complement. It is desirable to calcine the zeolite after base exchange. The metal cations that may be present include any of the cations that may be present include any of the cations of the metals of Groups I through VIII of the Periodic Table. However, in the case of Group IA metals, the cation content should in no case be so large as to substantially eliminate the activity of the zeolite for the catalysis being employed in the instant invention. For example, a completely sodium exchanged H-ZSM-5 appears to be largely inactive for shape selective conversions required in the present invention.

In a preferred aspect of this invention, the zeolites useful as catalysts herein are selected as those having a crystal framework density, in the dry hydrogen form, of not substantially below about 1.6 grams per cubic centimeter. It has been found that zeolites which satisfy all three of these criteria are most desired. Therefore, the preferred catalysts of this invention are those comprising zeolite having a constraint index as defined above of about 1 to 12, a silica to alumina ratio of at least about 12 and a dried crystal density of not substantially less than about 1.6 gram per cubic centimeter. The dry density for known structures may be calculated from the number of silicon plus aluminum atoms per 1000 cubic Angstroms, as given, e.g., on page 19 of the article on Zeolite Structure by W. M. Meier. This paper, the entire contents of which are incorporated herein by reference, is included in "Proceedings of the Conference Molecular Sieves, London, April 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density of course must be associated with a relatively small amount of free space within the crystal, which might be expected to result in more stable structures. This free space, however, seems to be important as the locus of catalytic activity.

Crystal framework densities of some typical zeolites including some which are not within the purview of this invention are:

| Zeolite | Void Volume | Framework Density |
| --- | --- | --- |
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

The intimate mixture of heterogeneous catalysts may be prepared in various ways. The two components may be separately prepared in the form of catalyst particles such as pellets or extrudates, for example, and simply mixed in the required proportions. The particle size of the individual component particles may be quite small, for example, from about 20 to about 150 microns, when intended for use in fluid bed operation; or they may be as large as up to about ½ inch for fixed bed operation. Or, the two components may be mixed as powders and formed into pellets or extrudate, each pellet containing both components in substantially the required proportions. Binders such as alumina, zirconia, silica, titania, magnesia, etc., may be present. Alumina is particularly preferred because, as shown by the Examples, it has a desirable catalytic effect on the synthesis gas conversion. Alternatively, the ZnO-Cr₂O₃ component that has catalytic activity for the reduction of carbon monoxide may be formed on the acidic crystalline aluminosilicate component by conventional means such as impregnation of that solid with salt solution of the desired metals, followed by drying and calcination. Base exchange of the acidic crystalline aluminosilicate component also may be used in some selected cases to effect the introduction of part or all of the carbon monoxide reduction component. Other means for forming the intimate mixture may be used, such as: precipitation of the carbon monoxide reduction component in the presence of the acidic crystalline aluminosilicate; or electroless deposition of metal on the zeolite; or deposition of metal from the vapor phase. Various combinations of the above preparative methods will be obvious to those skilled in the art of catalyst preparation. It should be cautioned, however, to avoid techniques likely to reduce the crystallinity of the acidic crystalline aluminosilicate.

It will be recognized from the foregoing description that the heterogeneous catalysts, i.e., the above-described intimate mixtures, used in the process of this invention, may have varying degrees of intimacy. At one extreme, when using ½ inch pellets of the ZnO-Cr₂O₃ carbon monoxide reducing component mixed with ½ inch pellets of the acidic crystalline aluminosilicate, substantially all locations within at least one of the components will be within not more than about ½ inch of some of the other component, regardless of the proportions in which the two components are used. With different sized pellets, e.g., ½ inch and ¼ inch, again substantially all locations within at least one of the components will be within not more than about ½ inch of the other component. These examples illustrate the lower end of the degree of intimacy required for the practice of this invention. At the other extreme, one may ball mill together acid crystalline aluminosilicate particles of about 0.1 micron particle size with chromia with or without zinc oxide of similar particle size followed by pelletization. For this case, substantially all the locations within at least one of the components will be within not more than about 0.1 micron of some of the other component. This exemplifies about the highest degree of intimacy that is practical. The degree of intimacy of the physical mixture may also be expressed as the minimum distance of separation of the central points located within the particles of the two components. This will, on average, be represented by one-half the sum of the average particle size for the two components. Thus, for the foregoing example illustrating the highest degree of intimacy, the centers of the particles of either of the two components will be separated from the nearest particle of the other component by an average distance of at least about 0.1 micron. The degree of intimacy of the heterogeneous catalyst is largely determined by its method of preparation, but it may be independently verified by physical methods such as visual observations, examination in an ordinary microscope or with an electron microscope, or by electron microprobe analysis.

In the process of this invention, synthesis gas is contacted with the heterogeneous catalyst at a temperature in the range of from about 400° F. to about 1000° F., preferably from about 500° F. to about 900° F., at a pressure in the range of from about 1 to about 1000 atmospheres, preferably from about 10 to about 300 atmospheres, and at a volume hourly space velocity in the range of from about 500 to about 50,000 volumes of gas, at standard temperature and pressure per volume of catalyst, or equivalent contact time if a fluidized bed is used. The heterogeneous catalyst may be contained as a fixed bed, or a fluidized bed may be used. The product stream containing hydrocarbons, unreacted gases and steam may be cooled and the and the hydrocarbons recovered by any of the techniques known in the art, which techniques do not constitute part of this invention. The recovered hydrocarbons may be further separated by distillation or other means to recover benzene, toluene, xylenes, or other aromatic hydrocarbons.

EXAMPLES 1–13

Synthesis gas having a H₂/CO ratio of 1 was reacted at 1200 psig, 800° F., and about 1 WHSV over a series of catalysts. The catalysts were prepared by coprecipitation of zinc-chromium nitrate solutions with NH₃. The catalysts containing alumina (Examples 1–6 and 10–13) were prepared by introducing alumina to the solution as the nitrate or acetate before precipitation. The precipitates were washed, dried at 100° C., calcined in air overnight at 538° C., combined with HZSM-5, and then pelletized. Exposing the prepared catalyst to flowing gas (H₂CO=1) at operating conditions (1200 psig, 800° F.) overnight was sufficient for activation. Results and catalyst compositions are described in Table I. Catalyst components of 60/80 mesh size were pelleted and re-sized by grinding to provide catalyst particles of 10/30 mesh particle size.

In Examples 1–4 and 6 (see Table I), the Zn to Cr ratio was varied while maintaining a constant Cr to Al ratio. Conversions and selectivities are plotted against the atom percent of Zn and Cr (Al- and ZSM-5-free basis) in FIG. 1. The composition of a typical commercial zinc chromite methanol synthesis catalyst (Harshaw Zn-0302) is also indicated on FIG. 1. It can be seen from the plot that aromatics selectivity is a strong function of the Zn/Cr ratio, and that virtually no aromatics are formed at Zn/Cr ratios optimized for methanol synthesis. As the Cr content increases, aromatics content rises sharply and passes through a maximum. An inverse correlation of conversion and aromatics selectivity is evident, indicating that aromatization is slower than the competitive hydrogenation reactions under the reaction conditions. Only traces of methanol or dimethyl ether were detected in the product. A typical aromatics distribution is shown in Table II; the overall distribution is 84.4 percent $A_6$-$A_{10}$ (8.5 percent durene) and 15.6 percent $A_{11}+$.

The effect of changing the Zn/Cr ratio at constant Al can be seen from the results of Examples 4, 11, and 12 in Table I. The effect is almost identical to that shown in FIG. 1 for the relationship between the Zn/Cr ratio and the Cr/Al ratio.

Figure 2:
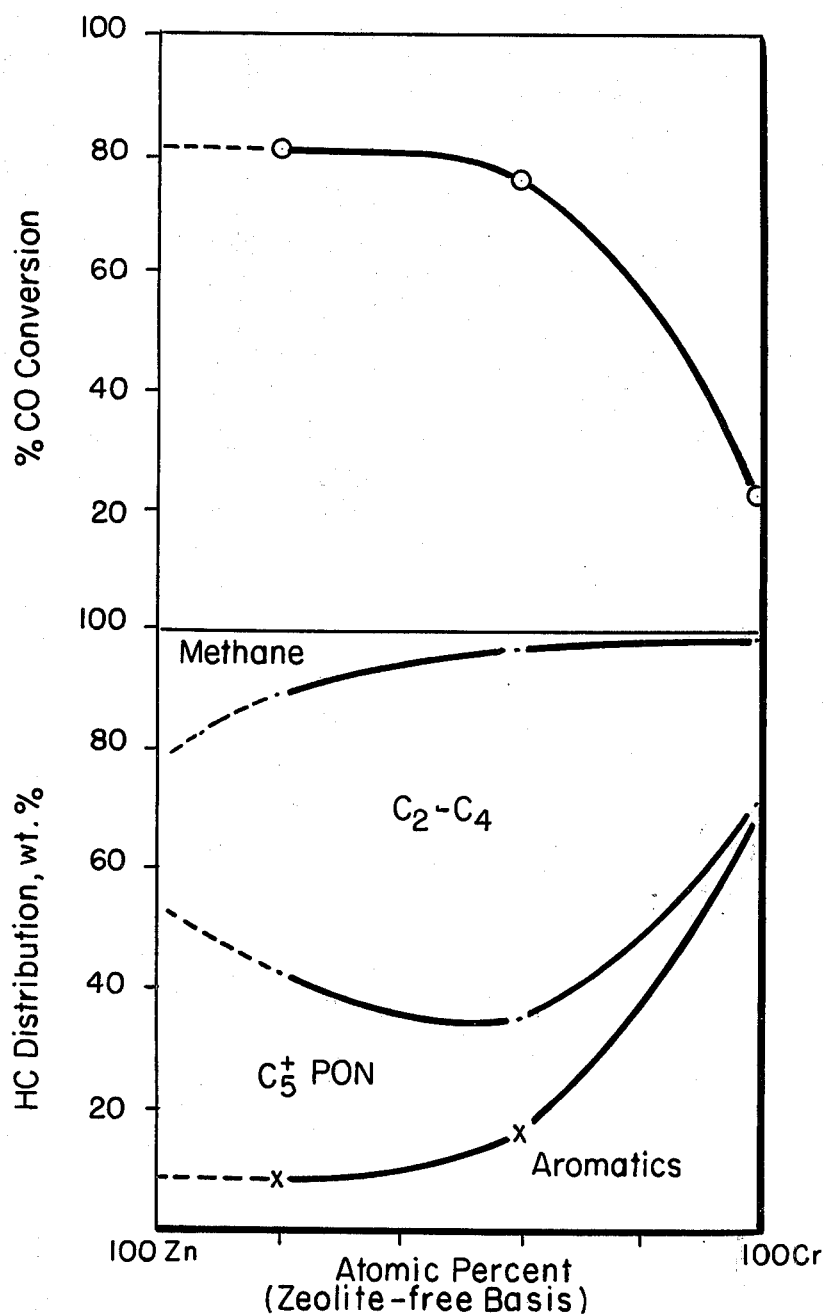

Examples 7–9 in Table I show the effect of the Zn/Cr ratio in the absence of Al. FIG. 2 is a plot of conversions and selectivities as a function of the atom percent of Zn and Cr (again on an Al- and ZSM-5 free basis). Completely different correlations from those of FIG. 1 are evident but indicate that Al has a catalytic function and is not simply an inert diluent.

Figure 3:
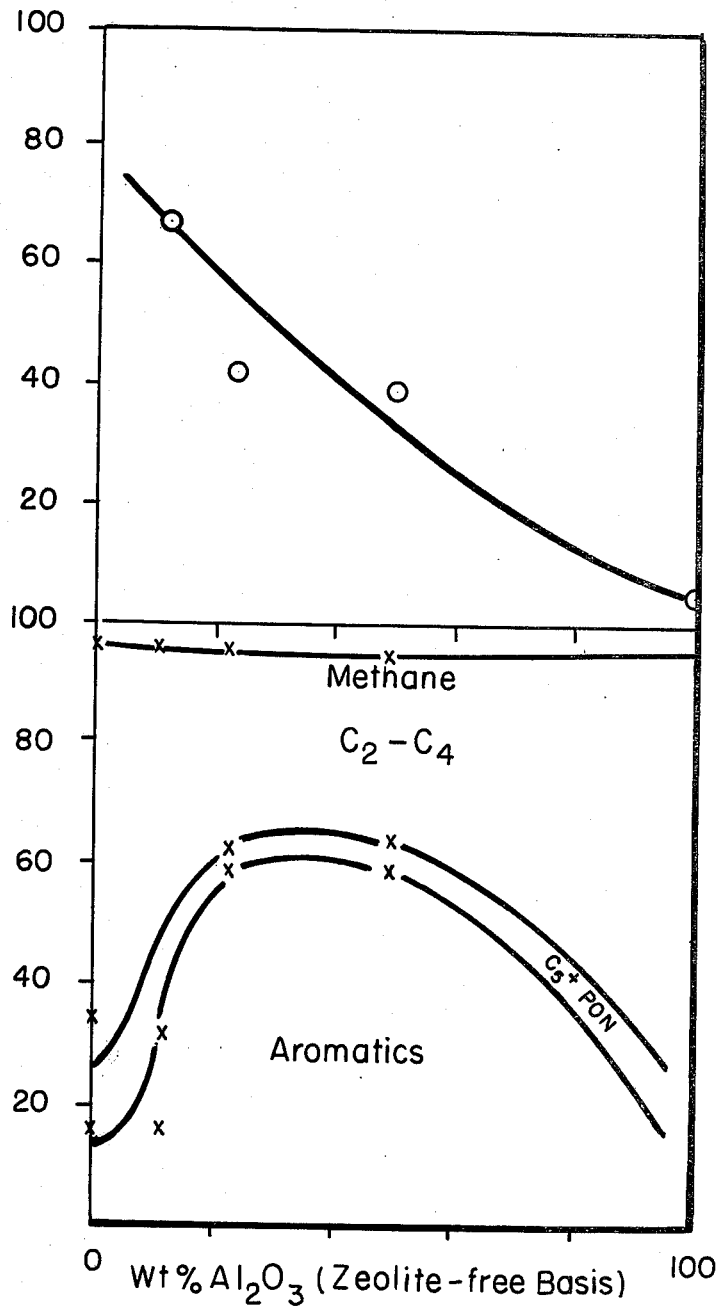

The effect of Al content at a constant Zn/Cr ratio is shown by Examples 4, 8, 10, and 13 and is plotted in FIG. 3. The aromatic selectivity maximum is again apparent and is further evidence that Al plays an active role.

Air regenerability of the catalyst composition of this invention was qualitatively demonstrated on one catalyst sample: the spent catalyst from Example 4 was placed in a muffle furnace and calcined in air at 1000° F. overnight. The catalyst was retested (see Example 5, Table I) and showed a 5 percent loss in CO conversion activity.

TABLE III

Syngas Conversion over ZnCr ZSM-5 — Effect of Zirconia

| RUN LPA- | 308 A | 307 A | 305 B |
|---|---|---|---|
| CATALYST COMP'N, PTS. | | | |
| ZnO | 0.03 | 0.46 | 0.21 |
| $Cr_2O_3$ | 0.56 | 0.13 | 0.38 |
| $ZrO_2$ | 0.31 | 0.31 | 0.31 |

TABLE I

Syngas Conversion Over ZnCrZSM-5—Effect of Alumina

| EXAMPLE | 1 | 2 | 3 | 4 | 5 | 6 | 7 | 8 | 9 | 10 | 11 | 12 | 13 |
|---|---|---|---|---|---|---|---|---|---|---|---|---|---|
| RUN LPA - | 282 A | 291 A | 294 A | 302 A | 302-R1A | 300 A | 257 A | 313 A | 299 A | 319 A | 316 A | 317 A | 318 A |
| CATALYST COMP'N, WT | | | | | | | | | | | | | |
| ZnO | 0.03 | 0.10 | 0.16 | 0.27 | 0.27 | 0.61 | 0 | 0.36 | 0.70 | 0.31 | 0.53 | 0.04 | 0.11 |
| $Cr_2O_3$ | 0.52 | 0.48 | 0.44 | 0.41 | 0.41 | 0.17 | 0.83 | 0.54 | 0.20 | 0.48 | 0.15 | 0.64 | 0.28 |
| $Al_2O_3$ | 0.35 | 0.32 | 0.30 | 0.22 | 0.22 | 0.12 | 0 | 0 | 0 | 0.11 | 0.22 | 0.22 | 0.44 |
| ZSM-5 | 0.10 | 0.10 | 0.10 | 0.10 | 0.10 | 0.10 | 0.17 | 0.10 | 0.10 | 0.10 | 0.10 | 0.10 | 0.10 |
| REACTION CONDITIONS | | | | | | | | | | | | | |
| T°F. | — | — | — | — | — | 800 | — | — | — | — | — | — | — |
| P, psig | — | — | — | — | — | 1200 | — | — | — | — | — | — | — |
| $H_2$/CO | — | — | — | — | — | 1 | — | — | — | — | — | — | — |
| GRSV, $hr^{-1}$ | 1490 | 1690 | 1690 | 1830 | 1820 | 2050 | 1680 | 1840 | 2845 | 2020 | 2450 | 1750 | 1840 |
| WHSV, $hr^{-1}$ | 1.0 | 1.1 | 1.0 | 1.1 | 1.1 | 1.1 | 1.0 | 1.2 | 1.8 | 1.0 | 1.2 | 0.9 | 1.0 |
| TOS, hr | 19 | 19 | 19 | 19 | 20 | 16 | 19 | 18 | 19 | 20 | 19 | 12 | 20 |
| CONVERSION, % | | | | | | | | | | | | | |
| CO | 66.4 | 55.9 | 46.9 | 41.6 | 36.4 | 84.6 | 23.5 | 74.9 | 79.8 | 67.1 | 79.2 | 54.3 | 39.6 |
| $H_2$ | 26.3 | 34.7 | 31.2 | 24.2 | 62.4 | 21.4 | 56.5 | 64.6 | 51.3 | 51.6 | 32.1 | 15.3 | |
| HC YIELD, % C | 37.0 | 26.6 | 23.3 | 17.8 | 16.1 | 45.8 | 16.2 | 39.4 | 42.8 | 35.7 | 42.3 | 25.1 | 19.1 |
| HC DISTRIBUTION, WT % | | | | | | | | | | | | | |
| Methane | 2.1 | 3.1 | 3.3 | 3.4 | 2.3 | 6.7 | 2.0 | 3.1 | 7.0 | 3.2 | 7.4 | 3.2 | 4.2 |
| Ethane | 26.5 | 15.6 | 15.1 | 12.6 | 16.2 | 15.1 | 12.2 | 8.8 | 15.4 | 9.7 | 10.7 | 10.9 | 9.6 |
| Ethylene | 0.1 | 0.2 | 0.2 | 0.2 | 0.3 | 0.2 | 0.3 | 0.1 | 0.1 | 0.1 | 0.2 | — | 0.2 |
| Propane | 13.2 | 15.8 | 15.0 | 15.6 | 13.1 | 17.5 | 8.8 | 26.3 | 13.6 | 28.9 | 14.9 | 27.6 | 15.1 |
| Propylene | <0.1 | 0.1 | 0.1 | 0.1 | 0.1 | 0.1 | 0.1 | 0.1 | 0.1 | 0.1 | 0.1 | — | 0.1 |
| Butanes | 6.1 | 6.6 | 6.0 | 5.6 | 4.7 | 27.0 | 4.4 | 26.9 | 21.6 | 26.7 | 25.4 | 13.1 | 7.2 |
| Butenes | — | — | — | — | — | — | — | — | — | — | — | — | — |
| $C_5$ + PON | 10.3 | 4.4 | 3.7 | 4.1 | 3.3 | 27.1 | 2.5 | 18.6 | 33.9 | 16.3 | 34.2 | 6.5 | 4.5 |
| Aromatics | 41.7 | 54.2 | 56.6 | 58.4 | 60.0 | 6.3 | 69.7 | 16.1 | 8.3 | 15.0 | 7.1 | 38.7 | 59.1 |

TABLE II

Aromatics Distribution
Example 4

| | Wt.% |
|---|---|
| Benzene | <0.1 |
| Toluene | 2.0 |
| Ethylbenzene | 0.1 |
| Xylenes | 12.1 |
| Tri Me benzenes | |
| 1, 2, 3 | 3.4 |
| 1, 2, 4 | 26.3 |
| 1, 3, 5 | 10.1 |
| Tetra Me benzenes | |
| 1, 2, 3, 4 | 3.6 |
| 1, 2, 3, 5 | 17.0 |
| 1, 2, 4, 5 (durene) | 8.5 |
| Other $A_{10}$ | 1.3 |
| $A_{11}$+ | 15.6 |
| | 100.0 |

(Table III continued)

| | 308 A | 307 A | 305 B |
|---|---|---|---|
| ZSM-5 | 0.10 | 0.10 | 0.10 |
| REACTION CONDITIONS | | | |
| T°,F. | — | 800 | — |
| P, psig | — | 1200 | — |
| $H_2$/CO | — | 1 | — |
| GHSV, $hr^{-1}$ | 1670 | 2880 | 2320 |
| WHSV, $hr^{-1}$ | 1.1 | 1.4 | 1.0 |
| TOS, hr | 18 | 18 | 24 |
| CONVERSION, % | | | |
| CO | 61.8 | 83.0 | 71.6 |
| $H_2$ | 36.2 | 68.0 | 50.7 |
| HC YIELD, % C | 34.2 | 45.9 | 53.5 |
| HC DISTRIBUTION, WT % | | | |
| Methane | 3.0 | 5.9 | 3.0 |
| Ethane | 19.7 | 13.1 | 11.7 |
| Ethylene | 0.1 | 0.2 | 0.1 |
| Propane | 19.8 | 13.6 | 21.2 |
| Propylene | 0.1 | 0.2 | 0.1 |
| Butanes | 9.1 | 22.1 | 24.3 |
| Butenes | — | — | — |
| $C_5$ + PON | 6.7 | 37.2 | 20.2 |
| Aromatics | 41.5 | 7.7 | 19.4 |

EXAMPLES 14-16

Figure 4:
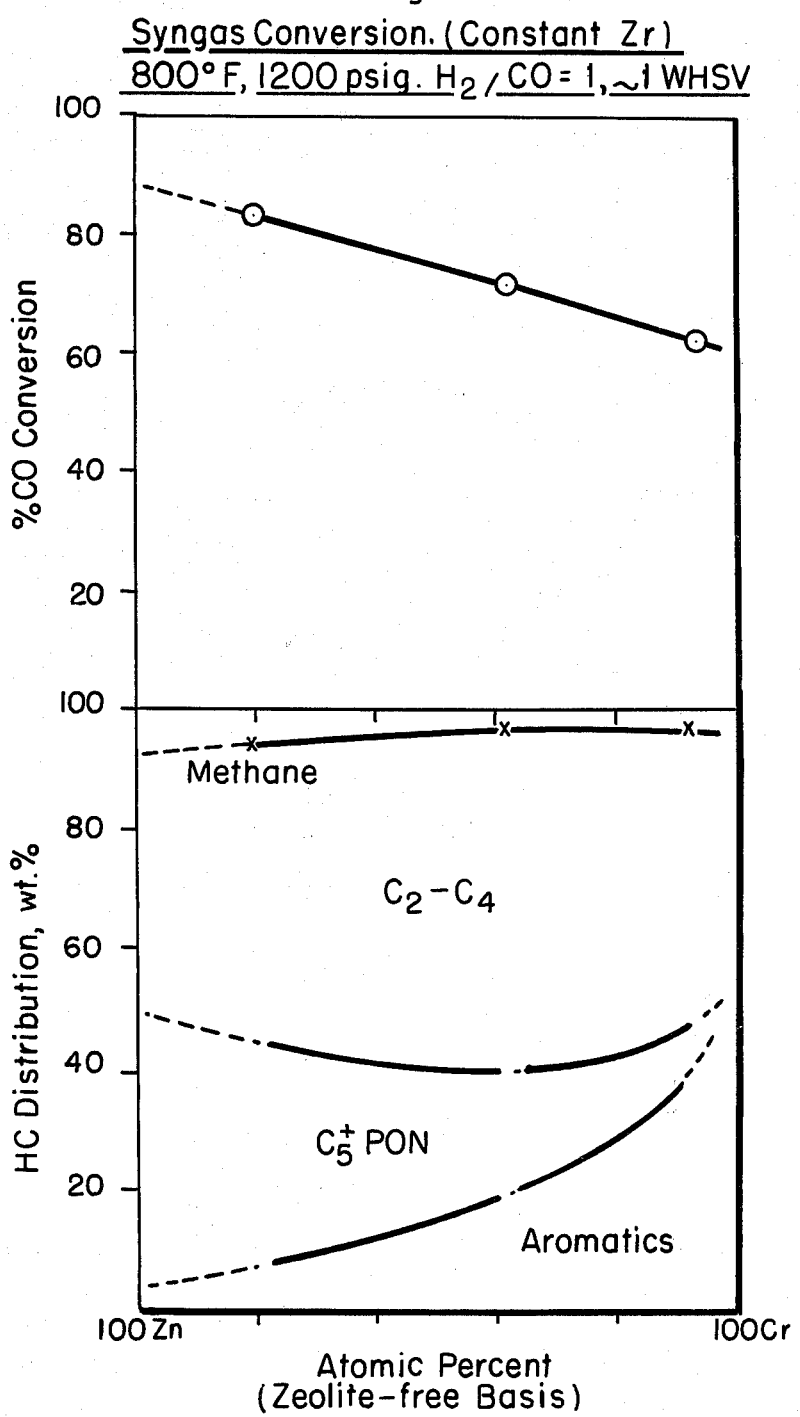

These examples are identical to the previous Examples except that zirconia was substituted for alumina as the binder for the intimate catalyst mixture. Results and catalyst compositions are shown in Table III and FIG. 4 is a plot of the results. The plot is similar to FIG. 2 (Al-free catalysts) and indicates that $ZrO_2$ has little or no catalytic effect on the zinc chromite catalyst.

A further significant aspect of this invention is the recognition that a methanol synthesis catalyst of the type hereinbefore defined will provide unexpectedly even more aromatic product components than hereinbefore recognized by the simple expedient of grinding the individual components of the final catalyst composition to an unusually fine state of subdivision less than 80 mesh such as to about 200 mesh or finer before mixing and pelleting the components to form particles of the catalyst composition. Generally, the pelleted catalyst particles will be in the range of 40 to 100 microns for use in a fluid catalyst operation and of larger particle size in the range of 10 to 30 mesh for a fixed catalyst bed operation.

In the following examples 17, 18 and 19, identified in Table IV below, synthesis gas ($H_2/CO=1$) was reacted at 1200 psig, 800° F. and passed at 1780 GHSV (gas hourly space velocity) over catalysts consisting of 16% ZnO, 44% $Cr_2O_3$, 30% $Al_2O_3$ and 10% HZSM-5 by weight. In example 17 (Run LPA 332A), the catalyst was a physical mixture of 60/80 mesh particles of each of the metal component and the ZSM-5 crystalline zeolite component. By 60/80 mesh is meant that the particles will pass through a 60 mesh screen but will be retained on an 80 mesh screen. In examples 18 and 19 (Runs LPA 328A and 328B respectively), the metal and HZSM-5 components were separately milled to (−200 mesh) and then mixed and pelleted to form particles of catalyst in the range of 10/30 mesh.

TABLE IV

| SYNGAS AROMATIZATION OVER Zn-Cr-Al/ZSM-5 $H_2/CO=1$, 1200 psig, 800° F. | | | |
| --- | --- | --- | --- |
| RUN LPA | 332A | 328A | 328B |
| Component Particle Size (Mesh) | 60/80 | 10/30 mesh particles formed from −200 mesh components | |
| GHSV, hr$^{-1}$ | 1780 | 1780 | 1740 |
| TOS, hr. | 19 | 19 | 42 |
| Conversion, mole % | | | |
| [$H_2$ + CO] | 44.1 | 37.7 | 32.9 |
| Hydrocarbons, wt.% | | | |
| Methane | 3.9 | 2.5 | 3.5 |
| Ethane | 12.8 | 12.2 | 13.6 |
| Ethylene | 0.3 | 0.1 | 0.6 |
| Propane | 22.6 | 9.9 | 9.4 |
| Propylene | 0.3 | <0.1 | 0.2 |
| Butanes | 15.5 | 3.3 | 4.2 |
| Butenes | — | — | — |
| $C_5$+ PON | 10.9 | 1.9 | 4.0 |
| Aromatics | 33.7 | 70.1 | 64.5 |
| Aromatics Distribution, wt % | | | |
| $A_6$–$A_{10}$ | 89.3 | 83.6 | 87.1 |
| $A_{11}$+ | 10.7 | 16.4 | 12.9 |

TABLE IV-continued

It will be observed from the data presented in Table IV that examples 18 and 19 produced higher yields of aromatics than the larger particle material used as catalyst in Run 17. It is thus concluded that for any given catalyst composition, preparing the catalyst from finer mesh component, finer than 80 mesh and more, preferably at least 200 mesh, provides a catalyst mixture having a greater selectivity for producing aromatics.

We claim:

1. In a process for forming hydrocarbons containing improved yields of aromatics by converting syngas comprising hydrogen and carbon oxides with a catalyst composition comprising a methanol synthesis catalyst component in admixture with a crystalline zeolite component comprising a silica-to-alumina ratio greater than 12, a pore dimension greater than about 5 Angstroms and a constraint index in the range of 1 to 12; the improvement which comprises admixing each of the components of the methanol catalyst comprising zinc, chromia and alumina and the crystalline zeolite component in a fine state of sub-division finer than 80 mesh and thereafter pelletizing the mixed finely ground material to form particles of the catalyst composition of a particle size in the range of 10 to 30 mesh.

2. The process of claim 1 wherein the methanol synthesis catalyst comprising zinc oxide and chromium oxide is in a Zn:Cr ratio less than 4:1.

3. The process of claim 1 wherein the catalyst composition comprises from 20 to 60 weight percent of alumina.

4. The process of claim 1 wherein the crystalline zeolite component of the catalyst composition is in an amount less than the methanol synthesis catalyst component.

5. The process of claim 1 wherein the individual catalyst components are about 200 mesh before mixing and pelleting.

* * * * *

UNITED STATES PATENT AND TRADEMARK OFFICE
CERTIFICATE OF CORRECTION

PATENT NO. : 4,188,336
DATED : February 12, 1980
INVENTOR(S) : CLARENCE D. CHANG & WILLIAM H. LANG It is certified that error appears in the above-identified patent and that said Letters Patent are hereby corrected as shown below:

In Abstract, line 4, "reduction of hydrogen" should be "reduction by hydrogen"
Col. 11-12, Table I, "GRSV" should be "GHSV"
Col. 11-12, Table I, "$H_2$": For Example 4, "24.2" should be "23.2";
　　　　　　　　　　　　　　　For Example 5, "62.4" should be "24.2";
　　　　　　　　　　　　　　　For Example 6, "21.4" should be "62.4";
　　　　　　　　　　　　　　　For Example 7, "56.5" should be "21.4";
　　　　　　　　　　　　　　　For Example 8, "64.6" should be "56.5";
　　　　　　　　　　　　　　　For Example 9, "51.3" should be "64.6";
　　　　　　　　　　　　　　　For Example 10, "51.6" should be "51.3";
　　　　　　　　　　　　　　　For Example 11, "32.1" should be "51.6";
　　　　　　　　　　　　　　　For Example 12, "15.3" should be "32.1";
　　　　　　　　　　　　　　　For Example 13, "15.3" should be inserted.

Col. 11, Table I, "$C_5$+ PON" should be "$C_5^+$ PON".
Col. 12, Table III, "$C_5$ + PON" should be "$C_5^+$ PON".
Col. 13, Table IV, "Hydrocarbons" should be underscored.
Col. 13, Table IV, "$C_5$+ PON" should be "$C_5^+$ PON".
Col. 13, Table IV, "Aromatics Distribution" should be underscored.

Signed and Sealed this

Fifth Day of August 1980

[SEAL]

Attest:

SIDNEY A. DIAMOND

Attesting Officer　　　Commissioner of Patents and Trademarks